United States Patent
Rao et al.

(10) Patent No.: US 11,913,887 B2
(45) Date of Patent: Feb. 27, 2024

(54) GRAIN SAMPLING AND IMAGING DEVICE

(71) Applicant: ZHEJIANG UNIVERSITY, Zhejiang (CN)

(72) Inventors: Xiuqin Rao, Zhejiang (CN); Yangyang Lin, Zhejiang (CN); Yitian Wang, Zhejiang (CN); Yanning Zhang, Zhejiang (CN); Xiaomin Zhang, Zhejiang (CN); Yibin Ying, Zhejiang (CN); Haiyi Jiang, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 448 days.

(21) Appl. No.: 17/287,113

(22) PCT Filed: Jun. 12, 2020

(86) PCT No.: PCT/CN2020/095776
§ 371 (c)(1),
(2) Date: Apr. 21, 2021

(87) PCT Pub. No.: WO2021/008284
PCT Pub. Date: Jan. 21, 2021

(65) Prior Publication Data
US 2021/0396681 A1    Dec. 23, 2021

(30) Foreign Application Priority Data
Jul. 18, 2019   (CN) .......................... 201910649986.8

(51) Int. Cl.
*G01N 21/85* (2006.01)
*G01N 15/02* (2006.01)
*G01N 33/02* (2006.01)

(52) U.S. Cl.
CPC .......... *G01N 21/85* (2013.01); *G01N 15/0227* (2013.01); *G01N 33/02* (2013.01); *G01N 2021/8592* (2013.01)

(58) Field of Classification Search
None
See application file for complete search history.

(56) References Cited

U.S. PATENT DOCUMENTS

| 4,194,634 | A | * | 3/1980 | Kelly | ...................... B07C 5/346 250/358.1 |
| 4,742,228 | A | * | 5/1988 | Bischoff | ............ G01N 21/4738 250/341.1 |
| 5,135,114 | A | * | 8/1992 | Satake | .................. B07C 5/3416 209/558 |

(Continued)

*Primary Examiner* — Kristina M Deherrera
*Assistant Examiner* — Mark A Shabman

(57) ABSTRACT

In a grain sampling and imaging device, a grain bin (1) is located under a sampling body (5), a grain feed connector (4) is fixed to a top of the sampling body (5), an observation window (2) is installed on the sampling body (5), a camera (3) is installed above the observation window (2); grains fall to a grain feed connector (4), and then into the sampling body (5), and then are sieved by multiple passages of the sampling body (5), a part of the grains randomly enter the observation window (2) and photographed by the camera (3), and finally all of the grains enter the grain bin (1) through a discharge outlet (5.1) provided at a bottom of the sampling body (5).

7 Claims, 4 Drawing Sheets

(56) References Cited

U.S. PATENT DOCUMENTS

| | | | | |
|---|---|---|---|---|
| 5,406,084 A * | 4/1995 | Tobler | ............... | G01N 21/4738 |
| | | | | 250/341.1 |
| 7,009,703 B2 * | 3/2006 | Canty | ............... | G01N 15/147 |
| | | | | 356/335 |
| 7,292,949 B2 * | 11/2007 | Ding | ............... | G01N 21/3563 |
| | | | | 209/555 |
| 8,569,644 B2 * | 10/2013 | Nierle | ............... | B07C 5/3425 |
| | | | | 250/341.7 |
| 8,620,059 B2 * | 12/2013 | Groves | ............... | G06T 7/0004 |
| | | | | 382/141 |
| 2004/0151360 A1 * | 8/2004 | Pirard | ............... | G01N 15/0227 |
| | | | | 382/110 |
| 2012/0171338 A1 * | 7/2012 | Hamid | ............... | G01N 21/85 |
| | | | | 356/402 |
| 2015/0375270 A1 * | 12/2015 | Ishizu | ............... | G01N 21/251 |
| | | | | 209/580 |
| 2016/0320311 A1 * | 11/2016 | Mishra | ............... | G01N 33/10 |
| 2019/0137382 A1 * | 5/2019 | Nasiou | ............... | G01N 21/85 |

* cited by examiner

GRAIN SAMPLING AND IMAGING DEVICE

CROSS REFERENCE OF RELATED APPLICATION

This is a U.S. National Stage under 35 U.S.C 371 of the International Application PCT/CN2020/095776, filed Jun. 12, 2020, which claims priority under 35 U.S.C. 119(a-d) to CN 201910649986.8, filed Jul. 18, 2019.

BACKGROUND OF THE PRESENT INVENTION

Field of Invention

The present invention relates to the field of sampling and imaging method and device, and more particularly to a grain sampling and imaging device.

Description of Related Arts

The grain sampling and imaging method is an important technology to achieve rapid, efficient and non-destructive testing of grains. Grain quality detection data and grain sampling data are important parameters support for crop harvest quality evaluation, crop breeding and grain quality evaluation.

Xi Tian et al. disclosed an agricultural seed quality detection device in 2018, including a primary quality inspection box, a quality control liquid, a filter grid, a floating seed recovery passage and a conveyor belt, which uses the nuclear magnetic resonance technology for detection (Xi Tian, Agricultural Seed Quality Detection Device [P]. Chinese Patent: CN 201820050656.8, filed on Jan. 12, 2018). Ping Lin et al. disclosed a soybean appearance quality detection device in 2019, including a metal black box, a processor, and another metal black box including a first variable-speed moving imaging component, which uses the variable-speed moving imaging component and changes the movement speed of the imaging component according to the reflectivity for detecting (Ping Lin, Soybean Appearance Quality Detection Device and Detection Method [P]. Chinese Patent: CN 201910255880.X, filed on Apr. 1, 2019). In recent years, the machine visual imaging technology is applied to grain detection. Xiaobo Zhang designed a corn grain mildew sampling detection system including a collection box, a camera and a light source (Xiaobo Zhang, Corn Grain Mildew Sampling Detection System Based on Image Technology: [Master thesis][D]. Hubei University of Technology, China in 2018). Xiaofang Shen et al. disclosed a fast detection method of broken rice rate based on image recognition, which uses the threshold segmentation method to detect the broken rice rate (Xiaofang Shen, Rapid Detection Method of Broken Rice Rate Based on Image Recognition [P]. Chinese Patent: CN 201811284303.5, filed on Oct. 31, 2018). Traditional grain sampling and testing is mainly based on manual sampling, but it has the disadvantages of high labor intensity and strong subjectivity in the detection process. Therefore, many scholars above use the grain detection methods and devices that combine machinery with control for grain detection. However, these methods are not suitable in the harvest production of grain sampling and imaging. The grain detection device that combines machinery with control is generally large in size and requires an additional external power source for driving. It is also easy to cause grain breakage during the detection process. The existing visual imaging method focuses on the research of the algorithm, and has not get rid of the mechanical structure of the external power source, and the lens is not closed during the imaging process, which makes it easy to be contaminated by impurities in the grains, resulting in misjudgment.

SUMMARY OF THE PRESENT INVENTION

In order to solve the problems in the background technology, an object of the present invention is to provide a grain sampling and imaging device. The device combines grain imaging with grain sampling, wherein a camera lens is sealed inside an observation passage. Through continuous random sampling and detecting throughout the whole process, real-time statistical analysis of grain quality data, such as rapid and efficient separation and counting of grains during actual production, is achieved. Moreover, the device is able to avoid contamination of the camera lens by grains.

The present invention adopts technical solutions as follows.

A grain sampling and imaging device comprises a grain bin, an observation window, a camera, a grain feed connector and a sampling body, wherein the grain bin is located under the sampling body, the grain feed connector is fixed to a top of the sampling body, the observation window is installed on the sampling body, the camera is installed above the observation window; grains fall to the grain feed connector, and then into the sampling body, and then are sieved by multiple passages of the sampling body, a part of the grains randomly enter the observation window and photographed by the camera, and finally all of the grains enter the grain bin through a discharge outlet provided at a bottom of the sampling body.

A multi-stage restricting port is provided in a middle of an upper portion of the sampling body for forming a feed inlet of the sampling body; multiple separation passages arranged inclined downwardly and an outlet passage vertically arranged are provided within the sampling body, the multiple separation passages are respectively defined as a first separation passage, a second separation passage, a detection passage and a recovery passage; an upper end of the first separation passage is communicated with an outlet provided at a lower end of the multi-stage restricting port, a first separation hole is provided in a bottom surface of a middle portion of the first separation passage, a lower end of the first separation passage is connected with an upper end of the outlet passage, the first separation passage is communicated with an upper end of the second separation passage through the first separation hole, a lower end of the second separation passage is connected with an upper end of the recovery passage in a turning manner, a second separation hole is provided in a bottom surface of a middle portion of the second separation passage, the second separation passage is communicated with an upper end of the detection passage through the second separation hole, a lower end of the detection passage and a lower end of the recovery passage are connected with a lower portion of the outlet passage, a lower end of the outlet passage penetrates through the sampling body for forming the discharge outlet of the sampling body; the transparent observation window is installed at a position of an outer wall of the sampling body where the detection passage is provided; two through slots are provided on a top surface of the middle portion of the first separation passage and a position of the bottom surface of the middle portion of the first separation passage below the first separation hole, respectively; an observation passage is provided between the two through slots, the camera passes through the two through slots and installed to the observation passage and faces towards the detection passage for photographing.

The multi-stage restricting port comprises a grain input port, a first-stage restricting port, a second-stage restricting port and a third-stage restricting port the latter three of which are provided within the grain input port from top to bottom in sequence; the grain input port, having a through-hole structure, is provided at a top surface of the sampling body; the first-stage restricting port, the second-stage restricting port and the third-stage restricting port have a trumpet-shaped structure, wherein an outer wall of an upper end of the trumpet-shaped structure of the first-stage restricting port is fixed to an inner wall of the grain input port, an inner diameter of a lower end of the trumpet-shaped structure of the first-stage restricting port, that of the second-stage restricting port and that of the third-stage restricting port are gradually decreased; an inner diameter of the upper end of the trumpet-shaped structure is larger than the inner diameter of the lower end of the trumpet-shaped structure.

The grain input port is funnel-shaped.

The observation window has a transparent pipe structure.

A fixed bracket for fixing the camera is installed at one side of the upper portion of the sampling body, a wire hole is provided in a side surface of the fixed bracket for allowing electric wires of the camera to pass through.

A support frame, having a hollow structure, is located at one side of the lower portion of the sampling body, multiple connection holes are provided in the support frame for accommodating bolts, the support frame is fixed with a top portion of the grain bin through the bolts, so that the sampling body is fixed with the grain bin through the bolts.

An opening is provided at one side of the grain bin, and the discharge outlet provided at the bottom of the sampling body is provided within the opening of the grain bin.

The sampling method provided by the present invention is continuous random sampling, which is able to realize continuous sampling and accurately obtain the grain data in any longer time interval during the sampling process according to image processing.

The present invention has some beneficial effects as follows.

Focusing on the grain quality detection system, according to physical external characteristics of the grains, such as grain size of rice, based on imaging technology for counting statistics and quality detection, a device is designed in the present invention. The device has good adaptability for grain separation and counting. After entering the multi-stage restricting port, the grains are restricted and guided in flow, and are divided into three separate streams within the sampling body. The overall sampling process has the characteristics of continuous random sampling. At the same time, the use of imaging technology to perform sampling imaging in the detection passage C is able to achieve rapid and efficient separation of grains in the actual production process, real-time statistical analysis of data and information such as counting, and is able to avoid contamination of the lens by the grains.

The experimental results show that the device provided by the present invention has high reliability, and is able to increase the speed of continuous sampling detecting of grains, which provides the engineering equipment and technical support for fast and efficient grain separation and counting.

Figure 1:
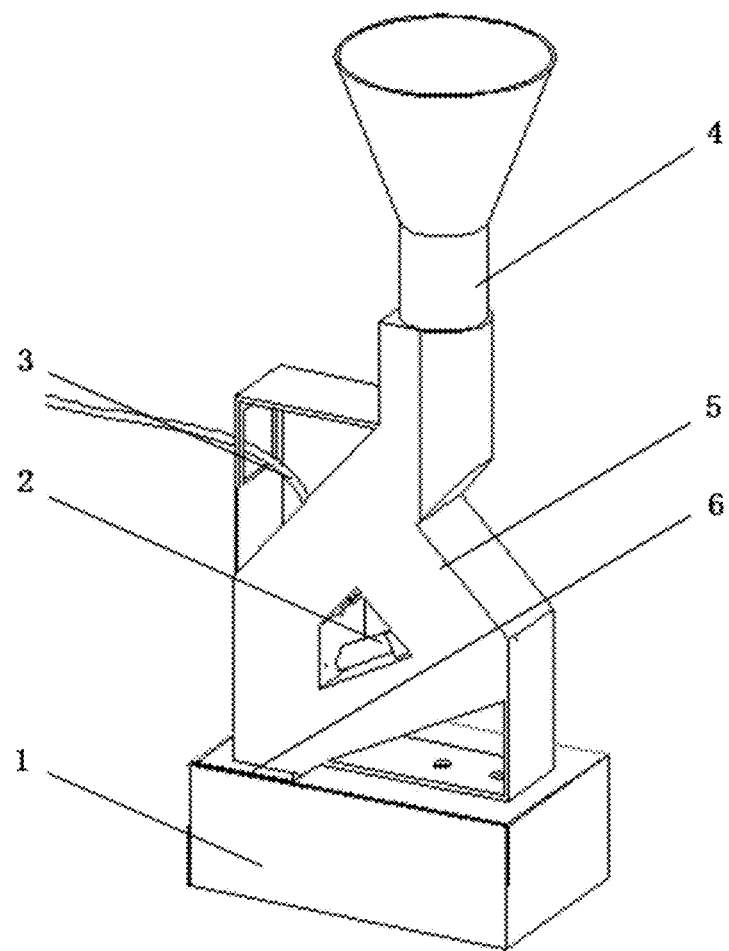
FIG. 1 is a structurally schematic view of a grain sampling and imaging device provided by the present invention.

In the drawings, 1: grain bin; 2: observation window; 3: camera; 4: grain feed connector; 5: sampling body; 5.1: discharge outlet; 5.2: installation hole for installing the camera; 5.3: wire hole; 5.4: fixed bracket; 5.5: multi-stage restricting port; 5.6: observation passage; 5.7: detection passage; 5.8: support frame; 5.9: retaining bolt hole; 5.10: first separation hole; 5.11: second separation hole; 5.12: outlet passage; 5.13: first through slot; 5.14: second through slot; 5.5.1: first-stage restricting port; 5.5.2: grain input port; 5.5.3: second-stage restricting port; 5.5.4: third-stage restricting port; 6: opening; A: first separation passage; B: second separation passage; C: detection passage; D: recovery passage.

DETAILED DESCRIPTION OF THE PREFERRED EMBODIMENT

The present invention is further described in detail with accompanying drawings and embodiments as follows.

Referring to FIG. 1 of the drawings, a grain sampling and imaging device according to a preferred embodiment of the present invention is illustrated, which comprises a grain bin 1, an observation window 2, a camera 3, a grain feed connector 4 and a sampling body 5, wherein the grain bin 1 is located under the sampling body 5, the grain feed connector 4 is fixed to a top of the sampling body 5, the observation window 2 is installed on the sampling body 5, the camera 3 is installed above the observation window 2; grains fall to the grain feed connector 4, and then into the sampling body 5, and then are sieved by multiple passages of the sampling body 5, a part of the grains randomly enter the observation window 2 and photographed by the camera 3, and finally all of the grains enter the grain bin 1 through a discharge outlet 5.1 provided at a bottom of the sampling body 5.

Figure 2:
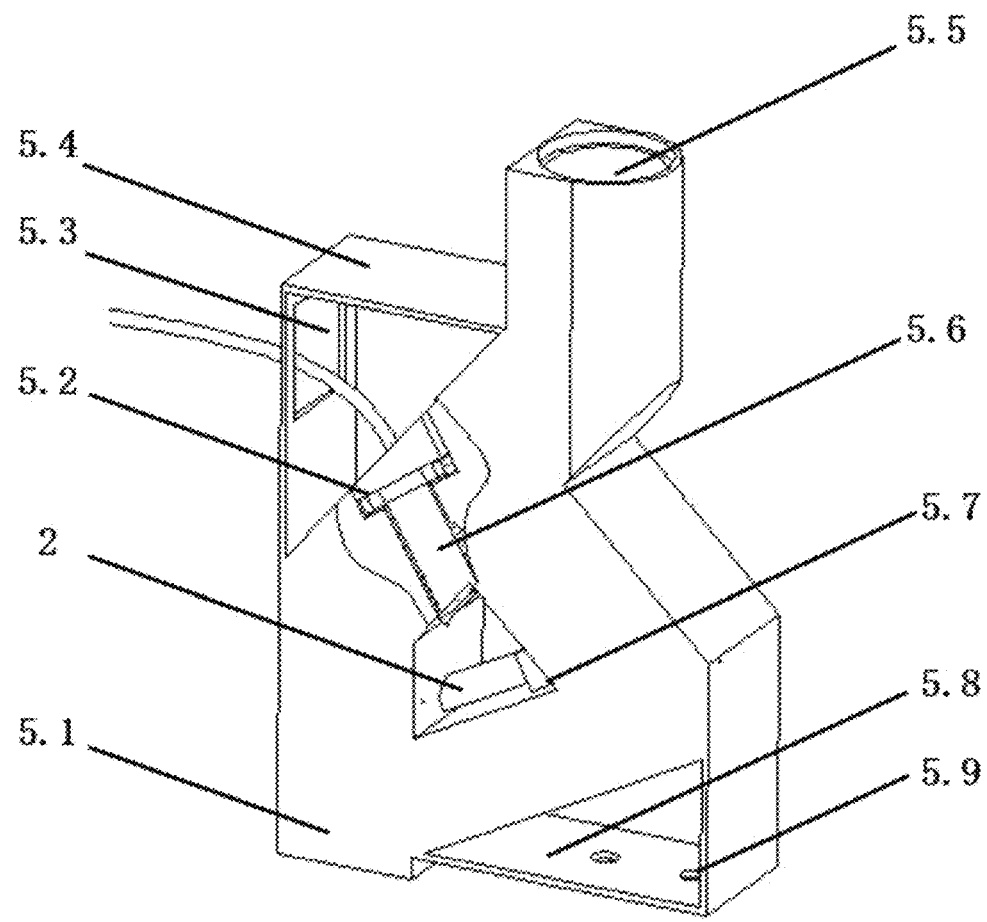
FIG. 2 is a structurally schematic view of a sampling body of the grain sampling and imaging device of the present invention.
Figure 4:
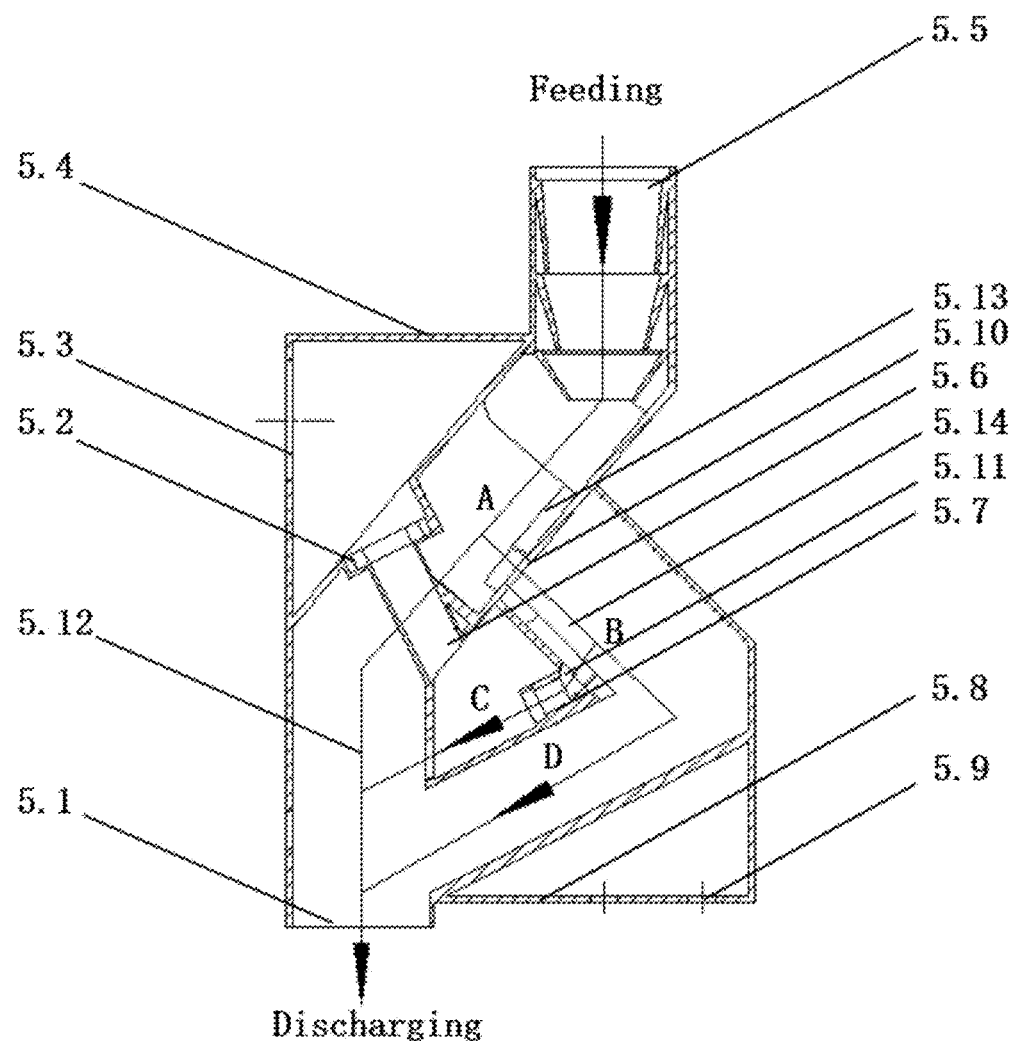
FIG. 4 is a semi-sectional view of the sampling body of the grain sampling and imaging device of the present invention.
Figure 5:
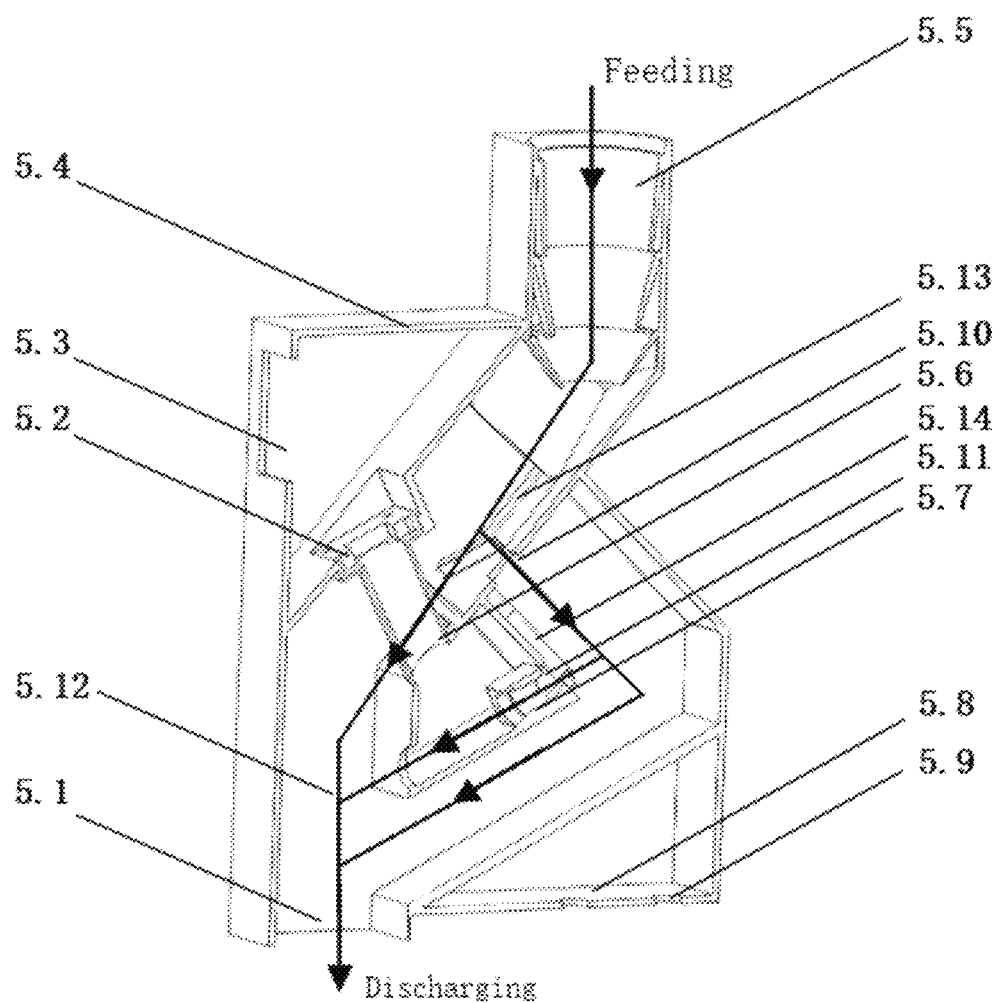
FIG. 5 is a three-dimensional schematic view of the sampling body of the grain sampling and imaging device of the present invention.

As shown in FIGS. 2, 4 and 5, a multi-stage restricting port 5.5 is provided in a middle of an upper portion of the sampling body 5 for forming a feed inlet of the sampling body 5, multiple separation passages arranged inclined downwardly and an outlet passage 5.12 vertically arranged are provided within the sampling body 5, the multiple separation passages are respectively defined as a first separation passage A, a second separation passage B, a detection passage C and a recovery passage D all of which are straight passages and are distributed across for forming a tree-shaped structure. An upper end of the first separation passage A is communicated with an outlet provided at a lower end of the multi-stage restricting port 5.5, a first separation hole 5.10 is provided in a bottom surface of a middle portion of the first separation passage A, a lower end of the first separation passage A is connected with an upper end of the outlet passage 5.12, the first separation passage A is communicated with an upper end of the second separation passage B through the first separation hole 5.10, a lower end of the second separation passage B is connected with an upper end of the recovery passage D in a turning manner, a second separation hole 5.11 is provided in a bottom surface of a middle portion of the second separation passage B, the second separation passage B is communicated with an upper end of the detection passage C through the second separation hole 5.11, the detection passage C and the recovery passage D are distributed in parallel, a lower end of the detection passage C and a lower end of the recovery passage D are connected with a lower portion of the outlet passage 5.12, a lower end of the outlet passage 5.12 penetrates through the sampling body 5 for forming the discharge outlet 5.1 of the sampling body 5.

Gaps are provided between two sides of the first separation hole 5.10 and inner walls of the first separation passage A; also, gaps are provided between two sides of the second separation hole 5.11 and inner walls of the second separation passage B, that is to say, a width of the first separation hole 5.10 and a width of the second separation hole 5.11 are smaller than a width of the first separation passage A and a width of the second separation passage B, respectively. Two circulation baffles are provided at the two sides of the first separation hole 5.10, respectively; and similarly, another two circulation baffles are provided at the two sides of the second separation hole 5.11, so that the grains flowing through the first separation passage A and the second separation passage B are able to pass through the first separation hole 5.10 and second separation hole 5.11, respectively.

The transparent observation window 2 is installed at a position of an outer wall of the sampling body 5 where the detection passage C is provided for collecting, detecting, sampling and imaging. The transparent observation window 2 has a transparent pipe structure.

Two through slots, namely, a first through slot 5.13 and a second through slot 5.14 are provided on a top surface of the middle portion of the first separation passage A and a position of the bottom surface of the middle portion of the first separation passage A below the first separation hole 5.10, respectively; an observation passage 5.6 is provided between the two through slots, the camera 3 passes through the two through slots and installed to the observation passage 5.6 and faces towards the detection passage C for photographing. Moreover, gaps are provided between two sides of the observation passage 5.6 and the inner walls of the first separation passage A, namely, a width of the observation passage 5.6 is smaller than the width of the first separation passage A, so that the grains flowing through the first separation passage A are able to pass through the gaps provided between the two sides of the observation passage 5.6 and the side edges of the first separation passage A.

An angle between the first separation passage A and a horizontal plane is 50°, an angle between the second separation passage B and the horizontal plane is 27°, after the observation window 2 is installed to the sampling body 5 in position, a straight line distance from a central axis of the observation window 2 to the camera 3 is 40 mm.

An outer diameter of the observation window 2 is fitted with an inner diameter of the second separation passage B, an outer diameter of the camera 3 is fitted with an inner diameter of the observation passage 5.6, the camera is installed in a sealed manner for avoiding contamination of the imaging lens by the grains, and an overall height of the sampling body 5 meets the requirements of a working machine.

Preferably, the grain feed connector 4 is funnel-shaped, the multi-stage restricting port 5.5 is for allowing and restricting the grains to enter the sampling body 5, the discharge outlet 5.1 is for outputting the grains which are sampled and separated.

As shown in FIG. 2, a fixed bracket 5.4 for fixing the camera 3 is installed at one side of the upper portion of the sampling body 5, a wire hole 5.3 is provided in a side surface of the fixed bracket 5.4 for allowing electric wires of the camera 3 to pass through, an outer diameter of a front-end lens of the camera 3 is fitted with the inner diameter of the observation passage 5.6, such that the camera 3 is able to observe lower view through the observation passage 5.6 via the observation window 2 without boundaries. A support frame 5.8, having a hollow structure, is located at one side of the lower portion of the sampling body 5, multiple retaining bolt holes 5.9 are provided in the support frame 5.8 for accommodating bolts, the support frame 5.8 is fixed with a top portion of the grain bin 1 through the bolts, so that the bottom portion of the sampling body 5 is fixed with the grain bin 1 through the bolts.

An opening 6 is provided at one side of the grain bin 1, the discharge outlet 5.1 provided at the bottom of the sampling body 5 is provided within the opening 6 of the grain bin 1, such that the grains passing through the sampling body 5 fall into the grain bin 1 through the opening 6 of the grain bin 1.

Figure 3:
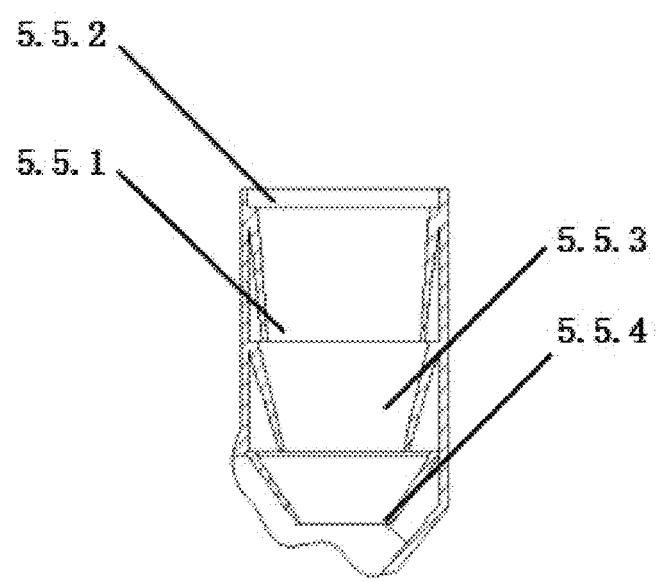
FIG. 3 is a semi-sectional view of a multi-stage restricting port of the grain sampling and imaging device of the present invention.

Referring to FIG. 3, the multi-stage restricting port 5.5 comprises a grain input port 5.5.2, a first-stage restricting port 5.5.1, a second-stage restricting port 5.5.3 and a third-stage restricting port 5.5.4 the latter three of which are provided within the grain input port 5.5.2 from top to bottom in sequence; the grain input port 5.5.2, having a through-hole structure, is provided at a top surface of the sampling body 5; the first-stage restricting port 5.5.1, the second-stage restricting port 5.5.3 and the third-stage restricting port 5.5.4 have a trumpet-shaped structure, wherein an outer wall of an upper end of the trumpet-shaped structure of the first-stage restricting port 5.5.1 is fixed to an inner wall of the grain input port 5.5.2, an inner diameter a lower end of the trumpet-shaped structure of the first-stage restricting port 5.5.1, that of the second-stage restricting port 5.5.3 and that of the third-stage restricting port 5.5.4 are gradually decreased, an inner diameter of the upper end of the trumpet-shaped structure is larger than the inner diameter of the lower end of the trumpet-shaped structure, so that the multi-stage restricting port 5.5 is able to control the flow and feeding speed of the inputted grains.

Referring to FIGS. 4 and 5, the grains are fed into the sampling body 5 through the multi-stage restricting port 5.5; the grains enter the grain feed connector 4, and then enter the first separation passage A after being restricted in flow by the multi-stage restricting port 5.5, flow through the first separation passage A to the first separation hole 5.10 for changing the movement direction of the grains; the grains are divided into two separate grain streams through the first separation hole 5.10, one of the two separate grain streams falls into the first separation hole 5.10 and then enters the second separation passage B, and another of the two separate grain streams flows through the gaps which are provided between the two sides of the first separation hole 5.10 and the inner walls of the first separation passage A, and the gaps which are provided between the two sides of the observation passage 5.6 and the inner walls of the first separation passage A in sequence, and then enters the outlet passage 5.12, and finally flows out of the outlet passage 5.12;

the one of the two separate grain streams flows through the second separation passage B to the second separation hole 5.11 for changing the movement direction of the one of the two separate grain streams; the one of the two separate grain streams is divided into two separate grain sub-streams through the second separation hole 5.11, one of the two separate grain sub-streams falls into the second separation hole 5.11 and then enters the detection passage C, and another of the two separate grain sub-streams flows through the gaps which are provided between the two sides of the second separation hole 5.11 and the inner walls of the second separation passage B, and then enters the recovery passage D, and then enters the outlet passage 5.12 through the recovery passage D, the finally flows out of the outlet passage 5.12;

the one of the two separate grain sub-streams entering the detection passage C, acts as sampling grain samples of the grains entering the grain feed connector 4, and is observed through the observation window 2; the camera located above the observation window 2 collects images of grains passing through the observation window, so as to achieve the purpose of sampling and detecting the grain imaging.

Grains flowing out of the outlet passage 5.12 enter the grain bin 1 through the discharge outlet 5.1.

From the implementation process, it is able to be seen that the overall sampling of the device provided by the present invention has characteristics of continuous random sampling, rapidity and high efficiency. Moreover, the sampling data obtained by the device of the present invention are more representative than ordinary discontinuous random sampling.

What is claimed is:

1. A grain sampling and imaging device, which comprises a grain bin (1), an observation window (2), a camera (3), a grain feed connector (4) and a sampling body (5), wherein:

the grain bin (1) is located under the sampling body (5), the grain feed connector (4) is fixed to a top of the sampling body (5), the observation window (2) is installed on the sampling body (5), the camera (3) is installed above the observation window (2) a multi-stage restricting port (5.5) is provided at a top end of the sampling body (5) for forming a feed inlet of the sampling body (5);

multiple separation passages arranged inclined downwardly and an outlet passage (5.12) vertically arranged are provided within the sampling body (5), the multiple separation passages are respectively defined as a first separation passage (A), a second separation passage (B), a detection passage (C) and a recovery passage (D);

an upper end of the first separation passage (A) is communicated with an outlet provided at a lower end of the multi-stage restricting port (5.5), a first separation hole (5.10) is provided in a bottom surface of a middle portion of the first separation passage (A), a lower end of the first separation passage (A) is connected with an upper end of the outlet passage (5.12), the first separation passage (A) is communicated with an upper end of the second separation passage (B) through the first separation hole (5.10), a lower end of the second separation passage (B) is connected with an upper end of the recovery passage (D), a second separation hole (5.11) is provided in a bottom surface of a middle portion of the second separation passage (B), the second separation passage (B) is communicated with an upper end of the detection passage (C) through the second separation hole (5.11), a lower end of the detection passage (C) and a lower end of the recovery passage (D) are connected with a lower portion of the outlet passage (5.12), a lower end of the outlet passage (5.12) penetrates through the sampling body (5) for forming a discharge outlet (5.1) of the sampling body (5);

the transparent observation window (2) is installed at a position of an outer wall of the sampling body (5) where the detection passage (C) is provided;

two through slots (5.13, 5.14) are provided on a top surface of the middle portion of the first separation passage (A) and a position of the bottom surface of the middle portion of the first separation passage (A) below the first separation hole (5.10), respectively; and an observation passage (5.6) is provided between the two through slots (5.13, 5.14), the camera (3) passes through the two through slots (5.13, 5.14) and is installed in the observation passage (5.6) and faces towards the detection passage (C) for photographing.

2. The grain sampling and imaging device according to claim 1, wherein the multi-stage restricting port (5.5) comprises a grain input port (5.5.2), a first-stage restricting port (5.5.1), a second-stage restricting port (5.5.3) and a third-stage restricting port (5.5.4) the latter three of which are provided within the grain input port (5.5.2) from top to bottom in sequence;

the grain input port (5.5.2), has a through-hole structure and is provided at a top surface of the sampling body (5);

the first-stage restricting port (5.5.1), the second-stage restricting port (5.5.3) and the third-stage restricting port (5.5.4) each have a trumpet-shaped structure, wherein an outer wall of an upper end of the trumpet-shaped structure of the first-stage restricting port (5.5.1) is fixed to an inner wall of the grain input port (5.5.2), an inner diameter of a lower end of the trumpet-shaped structure of the first-stage restricting port (5.5.1), that of the second-stage restricting port (5.5.3) and that of the third-stage restricting port (5.5.4) gradually decrease; and an inner diameter of the upper end of the trumpet-shaped structures is larger than the inner diameter of the lower end of the trumpet-shaped structures.

3. The grain sampling and imaging device according to claim 1, wherein the grain feed connector (4) is funnel-shaped.

4. The grain sampling and imaging device according to claim 1, wherein the observation window (2) has a transparent pipe structure.

5. The grain sampling and imaging device according to claim 1, wherein a fixed bracket (5.4) for fixing the camera is installed at one side of an upper portion of the sampling body (5), a wire hole (5.3) is provided in a side surface of the fixed bracket (5.4) for allowing electric wires of the camera (3) to pass through.

6. The grain sampling and imaging device according to claim 1, wherein a support frame (5.8), having a hollow structure, is located at one side of the lower portion of the sampling body (5), multiple retaining bolt holes (5.9) are provided in the support frame (5.8), and the support frame (5.8) is fixed with a top portion of the grain bin (1), so that the sampling body (5) is fixed with the grain bin (1).

7. The grain sampling and imaging device according to claim 1, wherein an opening (6) is provided at one side of the grain bin (1), and the discharge outlet provided at a bottom of the sampling body (5) is provided within the opening (6) of the grain bin (1).

* * * * *